(12) United States Patent
Steier et al.

(10) Patent No.: US 11,058,888 B1
(45) Date of Patent: Jul. 13, 2021

(54) MOUTH GUARD

(71) Applicant: Designs for Vision, Inc., Bohemia, NY (US)

(72) Inventors: Liviu Steier, Needham, MA (US); Richard E. Feinbloom, New York, NY (US)

(73) Assignee: Designs for Vision, Inc., Bohemia, NY (US)

( * ) Notice: Subject to any disclaimer, the term of this patent is extended or adjusted under 35 U.S.C. 154(b) by 0 days.

(21) Appl. No.: 17/070,307

(22) Filed: Oct. 14, 2020

Related U.S. Application Data

(60) Provisional application No. 63/075,438, filed on Sep. 8, 2020.

(51) Int. Cl.
*A61N 5/06* (2006.01)
*G08B 5/36* (2006.01)
*A63B 71/08* (2006.01)

(52) U.S. Cl.
CPC ......... *A61N 5/0603* (2013.01); *A61N 5/0624* (2013.01); *A63B 71/085* (2013.01); *G08B 5/36* (2013.01); *A61N 2005/0606* (2013.01); *A61N 2005/0626* (2013.01)

(58) Field of Classification Search
CPC ............... A61N 5/0603; A61N 5/0624; A61N 2005/0606; A61N 2005/0626; A61N 5/06–2005/073; A63B 71/085; G08B 5/36
See application file for complete search history.

(56) References Cited

U.S. PATENT DOCUMENTS

| | | | |
|---|---|---|---|
| 2004/0162549 A1* | 8/2004 | Altshuler | A61B 18/203 606/9 |
| 2009/0143842 A1* | 6/2009 | Cumbie | A61N 5/0624 607/88 |
| 2013/0280671 A1* | 10/2013 | Brawn | A61N 5/0603 433/24 |

* cited by examiner

*Primary Examiner* — Jonathan T Kuo
(74) *Attorney, Agent, or Firm* — Law Office of Carl Giordano, PC

(57) ABSTRACT

A mouth guard comprising a plurality of light sources is presented that provide for the emission of light in wavelength ranges that provide antiseptic benefits to a user, wherein the light outputted by the plurality of light sources are activated by a sensor configured to determine a proximity of the mouth guard to an object and generate a signal that is used to control the application of a voltage to the plurality of light sources, for a predetermined time period.

20 Claims, 4 Drawing Sheets

MOUTH GUARD

CLAIM OF PRIORITY

This application claims, pursuant to 35 USC 119, priority to and the benefit of the earlier filing date, of that provisional patent application filed on Sep. 8, 2020 and afforded Ser. No. 63/075,438, the contents of which are incorporated by reference herein.

FIELD OF THE INVENTION

This invention relates to the field of dentistry and more particularly to a mouth guard that provides sterilization of a patient's mouth.

BACKGROUND OF THE INVENTION

Research has found that the of the application of blue, ultra-violet or a combination of blue and ultra-violet light to a surface is an effective means for reducing the activity of virus and bacteria. Thus, it is useful for dental practitioners to apply light (e.g., blue and/or ultra-violet light) to a patient's mouth to reduce the likelihood of the patient contracting an infection from the virus and bacteria that are known to exist in the patient's mouth.

However, the applied light may be harmful to the human eye and, thus, eye protection is required for both the patient and the practitioner to avoid either party from inadvertently viewing the harmful light.

Hence, there is a need in the industry for applying a light therapy to a patient while preventing any inadvertent viewing of the applied light.

SUMMARY OF THE INVENTION

Disclosed is a mouth guard suitable for applying a light to a patient so as to reduce virus and bacteria within a patient's mouth.

Disclosed is a mouth guard for controlling the application of a light to a patient in a safe manner.

Disclosed is a mouth guard for the timed application of a light to a patient in a manner to avoid the inadvertent exposure of the patient's eyes to a light that may be harmful.

In accordance with the principles of the invention, a mouth guard is disclosed which comprises a flexible material to engage a patient's mouth and a circuit board comprising a plurality of light emitting diodes (LEDs) suitable for generating at least a light and an electrical circuit configured to control a voltage applied to the LEDs for a known period of time when the mouth guard is properly positioned on the patient.

BRIEF DESCRIPTION OF DRAWINGS

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

It is to be understood that the figures and descriptions of the present invention described herein have been simplified to illustrate the elements that are relevant for a clear understanding of the present invention, while eliminating for purposes of clarity, many other elements. However, because these omitted elements are well-known in the art, and because they do not facilitate a better understanding of the present invention, a discussion of such elements is not provided herein. The disclosure herein is directed also to variations and modifications known to those skilled in the art.

DETAILED DESCRIPTION

Figure 1:
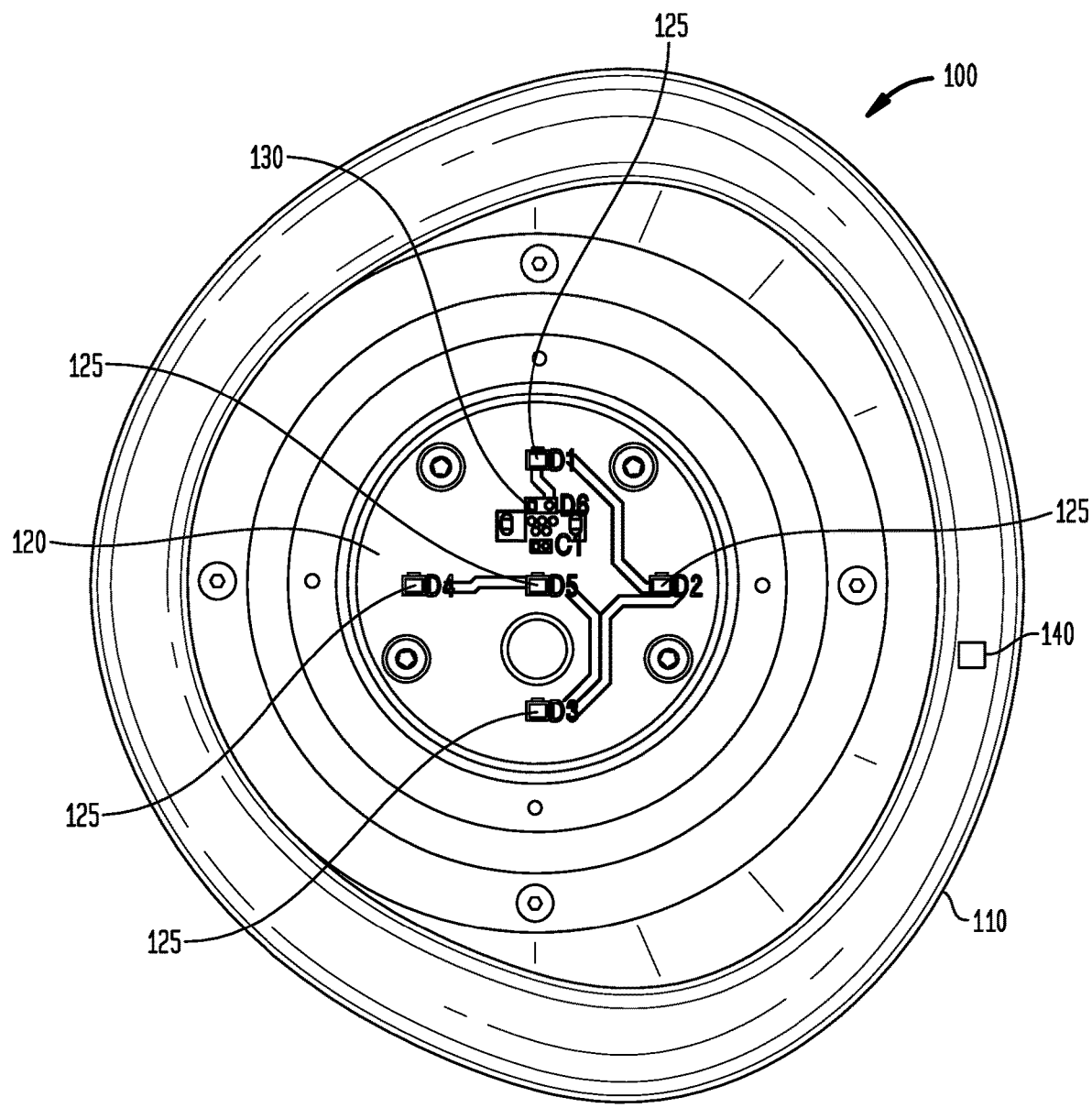
FIG. 1 illustrates a front view of an exemplary embodiment of a mouth guard in accordance with the principles of the invention.

FIG. 1 illustrates a front view and an exemplary embodiment of a mouth guard 100 in accordance with the principles of the invention.

In this exemplary embodiment, mouth guard 100 comprises a flexible cup element 110 suitable for engaging a surface surrounding the mouth of a user or a patient. The flexible cup element 110, which is attached to housing 410 (see FIG. 4), contains therein a printed circuit board 120 comprising a plurality of LEDs 125, wherein the LEDs 125 output a light, and an electronic circuit 130 configured to control the application of a voltage to LEDs 125. In accordance with the principles of the invention, the light may be in one or more known wavelength ranges; some of which may be harmful to a user. For example, the light generated by the LEDs 125 may be in one of an ultra-violet light wavelength range may be composed of one or more light wavelength ranges associated with UV-A (i.e., 320-400 nanometers (nm)), UV-B (290-320 nm) and UV-C (220-290 nm). Additionally, LEDs 125 may generate an ultra-violet light composed of wavelengths from 90-220 nm (i.e., Near UV and FAR UV). Similarly, the light generated by LEDs 125 may be in a blue wavelength range that extends from the upper limit of the UV wavelength range (e.g., 400 nm) to the generally accepted "blue" wavelength range (i.e., 450-495 nm). In this case, the term "blue light wavelength range" would further include the violet wavelength range of (i.e., 380-450 nanometers (nm)). In addition, LEDs 125 may generate light in a one or more light wavelength ranges such as 500-700 nm. Accordingly, in accordance with the principles of the invention, the LEDs 125 disclosed, herein, may be selected to generate light in at least one of a non-visible light wavelength range (e.g., UV) and in a visible light wavelength range (e.g., blue, green, yellow, etc.).

Further illustrated is sensor 140 incorporated into flexible cup element 110. Sensor 140 is configured to provide an indication to electronic circuit 130 that mouth guard 100 is appropriately positioned about the surface surrounding a user's mouth. In one aspect of the invention, sensor 140 may be a pressure or contact switch that provides an indication of the sensor being activated by its contact with a surface. In another aspect of the invention, sensor 140 may be an IR (infra-red) sensor that detects reflection of a transmitted signal to determine a distance to a surface and provide an indication the sensor is activated when the determined distance is substantially zero. In another aspect of the invention, sensor 140 may be a proximity sensor that detects the proximity of the sensor to the surface and provides an indication the sensor is activated when the determined proximity is zero or near zero. In another aspect of the invention, sensor 140 may be a heat-activated sensor, which measures a temperature. For example, a heat sensor may comprise an infra-red sensor that is suitable for determining the presence of a heat source. In this case, when sensor 140, in the form of an infra-red sensor, is placed close to, or in contact with, a patient, the body temperature of the patient may be measured by the infra-red sensor, and an indication of the placement of sensor 140 proximate to the patient may be transmitted to the electronic circuit 130.

In one aspect of the invention, the indication may represent a steady voltage level during a period between an initial contact (or determination of proximity) of said sensor with said object and a loss of contact (or determination of proximity) of said sensor with said object. In another aspect of the invention, the indication may represent a "one shot" (i.e., at least one pulse) indicating an initial contact (or determination of proximity) of said sensor with said object and a second "one shot" (i.e., at least one pulse) indicating a loss of contact (or determination of proximity) of said sensor with sensor.

Electronic circuit 130 in response to the indication of the appropriate position of mouth guard (i.e., proximity to, or in contact with, a user) initiates a timer (not shown) and concurrently applies a voltage, through a switch (not shown), to selected ones of the plurality of LEDs 125.

In one aspect of the invention the plurality of LEDs 125 may output a light having a substantially same wavelength (e.g., 405 nm) in at least one light wavelength range. In another aspect of the invention the plurality of LEDs 1245 may output a light at a plurality of different wavelengths (e.g., 405 nm and 450 nm; 405 nm and 650 nm, 600 nm and 650 nm, etc.) in at least one wavelength range.

In accordance with the principles of the invention, the output light intensity of the different wavelengths may be the same or may be different. For example, with a particular exemplary configuration, wherein a light at 405 nm and a light at 450 nm is outputted, the intensity of the light output at 450 nm may be less that the light intensity at 405 nm.

In accordance with the principles of the invention, the light of different wavelengths may be outputted concurrent or sequentially for the same amount of time or for different times. For example, and using an exemplary example of the output of 405 nm and 450 nm, the light at 405 nm may be outputted for a first time period and the light at 450 nm may be outputted for a second time period; the first and second time periods being one of the same and different. In addition, the first time period and the second time period may be initiated at the same time or at different times so that the 405 nm and the 450 nm lights may overlap in time. Alternatively, the first time period and the second time period may be selected such that the light outputted may be turned off at the same time. Alternatively, the second time period may not be initiated until the first time period has expired (i.e., disjoint light output). In addition, the light outputted by LEDs 125 may be sequenced to alternate the light output such that the light of a first LED may be turned on/off periodically, while the light of the second LED may be turned on during the off periods of the first LED. In accordance with the principles of the invention, the light output sequence may generally be one of: concurrent, overlapping or disjointed (i.e., non-overlapping).

Although five (5) LEDs 125 are shown, it would be recognized that the number of LEDs 125 and/or the wavelengths of the light that each of the LEDs 125 outputs may altered without altering the scope of the invention.

Figure 2:
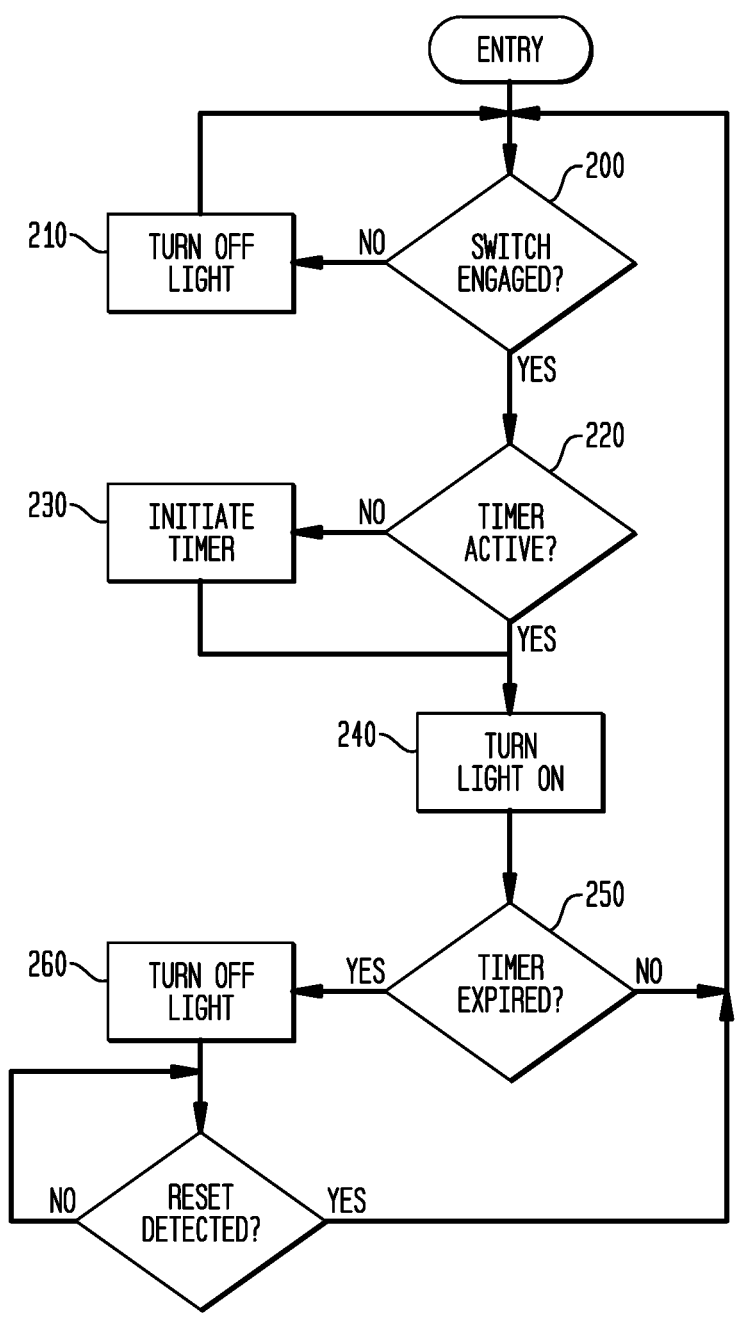
FIG. 2 illustrates a process for safely controlling the application of a blue and/or ultra-violet light to a patient.

FIG. 2 illustrates an exemplary process for safely controlling the application of a light to a user.

In accordance with the principles of the invention, a determination is made whether the sensor 140 is in contact with (or proximate to) with a user. If the answer is negative, then processing proceeds to step 210, where the voltage is removed from LEDs 125.

However, if the answer is in the affirmative, then processing proceeds to step 220, where a determination is made whether a timer is active. If the time is not active, then processing proceeds to step 230, where a countdown timer is initiated (for example, the timer may be initiated for a pre-determined time value, such as 2 minutes). Processing then proceeds to step 240, where a voltage is applied to LEDs 125.

Returning to step 220, if the timer is indicated as being active, processing proceeds to step 240, where the voltage is applied to LEDs 125. As discussed above the application of the voltage to the LEDs 125 may be such that the output of the light may be one of concurrent, overlapping and disjointed.

Processing then proceeds to step 250 where a determination is made whether the timer has expired (i.e., counted down to zero). If the timer has expired, the processing proceeds to step 260 where the voltage applied to LEDs 125 is removed. Otherwise, processing proceeds to step 200 where a determination is made whether the sensor 140 is engaged.

Figure 3:
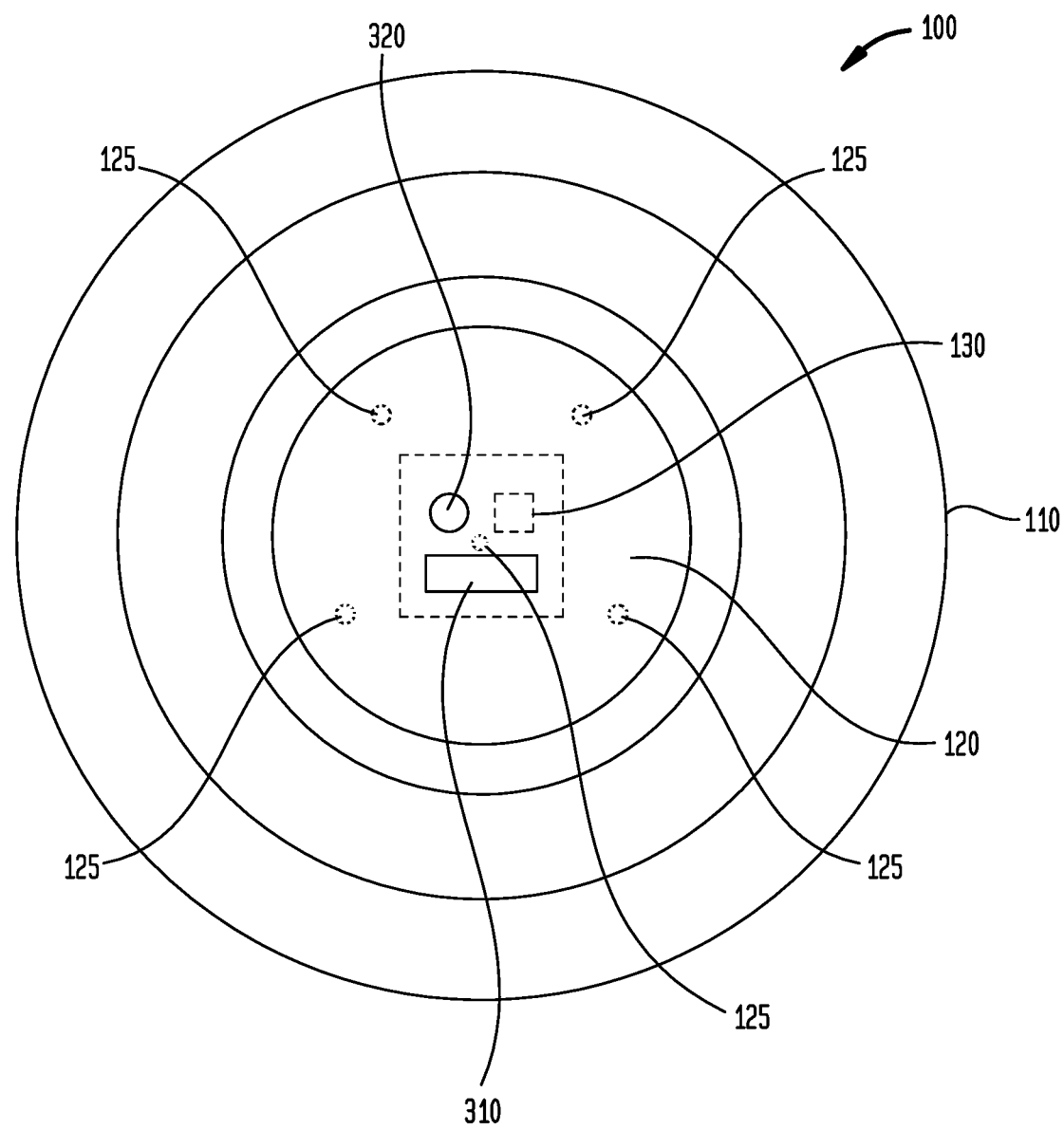
FIG. 3 illustrates a rear view of the exemplary embodiment of the mouth guard shown in FIG. 1.

FIG. 3 illustrates a rear view of the exemplary embodiment of the mouth guard 100 shown in FIG. 1.

In this illustrated embodiment, printed circuit board (PCB) 120 is illustrated within flexible mouth guard element 110. Further illustrated are LEDs 125 and electronic circuit 130, which are positioned on a front surface of PCB 120.

In this illustrated embodiment, a rear facing safety light 320 is provided. Rear facing safety light 320 provides a light output to provides an indication that a voltage has been applied to LEDs 125. For example, the light output by safety light 320 may be of one of a red, green, blue, for example, color.

In one aspect of the invention, safety light 320 may project a green light when a voltage is applied to LEDs 125 (i.e., when sensor 140 is active) and project a red light when the timer is active and sensor 140 is not active (i.e., voltage is removed from LEDs 125).

Safety light 320 may further represent a switch (e.g., a lighted switch), which when depressed resets the timer within electronic circuit 130. In this case, safety light 320 may project a white light, for example, to indicate mouth guard 100 is in a reset condition. For example, the depression of the lighted switch representing safety light 320 may reset a flag that indicates the timer is not active while resetting the timer. (see step 220, FIG. 2).

Although a reset switch has been discussed with regard to safety light 320, it would be recognized that safety light 320 may represent a one or more light emitting diodes suitable for generating different wavelengths (e.g., green, red, white) and a separate reset switch (not shown) may be incorporated onto PCB 120 without altering the scope of the invention. Similarly, the reset switch (whether a separate switch or incorporated into safety light 320) may further represent an ON/OFF switch to control the application of a voltage to electronic circuit 130, which controls the application of a voltage to LEDs 125, as previously discussed.

In accordance with another aspect of the invention, the safety light 320 may represent a light filter that allows for the passage of light having wavelengths that are non-harmful to the eye. In accordance with the principles of the invention, the light (whether blue and/or UV) generated by LEDs 125 may be blocked by safety light 320 by blocking wavelengths that may be harmful to the user. The illumination caused by the generation of light as seen through light filter of safety light 320 provides an indication of the light of LEDs 125 is being generated.

Further illustrated is power source 310 that provides a voltage to electronic circuit 130. Power source 310 may represent a constant direct current voltage source. For example, power source 310 may be a commercially available battery, such as alkaline or rechargeable battery. In another aspect of the invention, power source 310 may represent an input from a remote power source. For example, power source 310 may represent a USB (universal serial bus) connector that may supply a DC voltage, provided by a remote A/C to D/C converter. The USB port may further be used to provide power to recharge a rechargeable battery that may be used to provide a voltage to electronic circuit 130.

As would be appreciated, the voltage may be provided by a power source wired to the electronic circuit that generates a DC voltage or a battery attached to the mouth guard.

Figure 4:
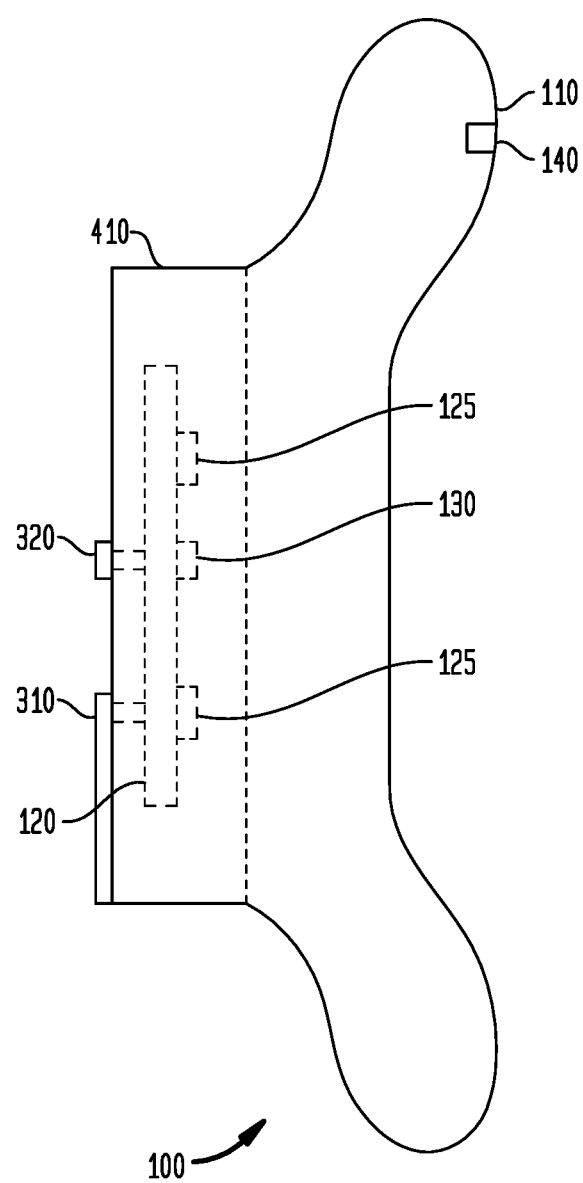
FIG. 4 illustrates a side view of the exemplary embodiment of the mouth guard shown in FIGS. 1 and 3.

FIG. 4 illustrates a side view of the exemplary embodiment of a mouth guard 100 in accordance with the principles of the invention.

In this illustrated embodiment, mouth guard 100 comprises flexible element 110, which is shaped to provide 360 degree coverage of an area of a patient (or user). For example, the user's mouth. Further illustrated is sensor 140 positioned along a leading edge of flexible element 110.

Flexible element 110 is attached to housing 410. Within housing 410 is shown PCB 120 including electronic circuit 130 and LEDs 125. Further illustrated are safety light 320 and battery or DC power source 310 in contact with PCB 120 and consequently electronic circuit 130.

In one aspect of the invention flexible element 110 may be removably attached to housing 410. The removability of flexible element 110 provides the benefit of deep clearing of flexible element 110 or for the interchangeability of flexible element 110 to accommodate different sizes of flexible element 110.

In summary, a mouth guard is disclosed that allows for the safe application of a blue and/or ultra-violet light to a user while limiting the potential of the user inadvertently viewing the blue and/or ultra-violet light. In accordance with the principles of the invention, a sensor provides an indication that the mouth guard is appropriately positioned, where the indication causes a timer to be initiated and further turns on the light emitting diodes, wherein the timer limits the total time the LED light is turned on. Thus, the lights are turned on only when the mouth guard is properly positioned and the timer is active. Once the mouth guard is not properly positioned or the timer is no longer active, the lights are turned off by the removal of a voltage to the LEDs.

Although exemplary wavelengths are disclosed, it would be appreciated that any combination of wavelengths may be selected based on their wavelength range being within known light ranges.

It would be appreciated that various modifications and changes can be made without departing from the scope of the invention as set forth in the claims. Accordingly, the specification is to be regarded in an illustrative manner, rather than with a restrictive view, and all such modifications are intended to be included within the scope of the invention. Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure.

It is expressly intended that all combinations of those elements that perform substantially the same function in substantially the same way to achieve the same results are within the scope of the invention. Substitutions of elements from one described embodiment to another are also fully intended and contemplated.

What is claimed is:
1. A mouth guard comprising:
   a cup shaped housing comprising:
      an open first end comprising:
         a flexible lip extending circumferentially along said open first end of said cup shaped housing, said flexible lip configured to engage a lower area of a face of a user;
         a sensor, embedded within said flexible lip, said sensor configured to:
      determine a proximity of said mouth guard to said lower area of said face; and a closed second end comprising:
  a printed circuit board comprising:
    a plurality of light emitting sources, wherein said plurality of light emitting sources are configured to:
      emit a light into a mouth of said user; and
    an electronic circuit configured to:
      receive from said sensor an indication of proximity of said mouth guard to said lower area of said face; and
      control an application of a voltage to said plurality of light emitting sources based on said received indication of proximity.

2. The mouth guard of claim 1, further comprising:
  an indicator configured to:
    illuminate in response to said received indication of proximity.

3. The mouth guard of claim 2, wherein said indicator comprises at least one of:
  a light emitting diode and a filter panel.

4. The mouth guard of claim 3, wherein said at least one of said light emitting diode associated with said indicator is one of: a multi-color light emitting diode, a red light emitting diode, a green light emitting diode and a white color light emitting diode.

5. The mouth guard of claim 1, wherein said sensor comprises one of: a contact sensor, an IR transmitter/detector sensor, a proximity sensor and a heat sensor.

6. The mouth guard of claim 1, further comprises:
  a means for applying said voltage to said electronic circuit, said means comprising one of: a rechargeable battery, a standard battery and a remote power source.

7. The mouth guard of claim 1, wherein said plurality of light emitting sources comprises at least one of: a light emitting diode emitting light in a blue wavelength range, a light emitting diode emitting light in an ultra-violet wavelength range and a light emitting diode emitting light in a visible wavelength range.

8. The mouth guard of claim 1, wherein said plurality of light emitting sources output a light having a substantially same wavelength.

9. The mouth guard of claim 1, wherein said plurality of light emitting sources output a light having different wavelengths.

10. The mouth guard of claim 1, wherein said plurality of light emitting sources output light at different light intensity.

11. The mouth guard of claim 1, wherein said plurality of light emitting sources output light concurrently.

12. The mouth guard of claim 1, wherein said plurality of light emitting sources output light at different start times and for different time periods.

13. The mouth guard of claim 1, wherein said electronic circuit comprises:
  a timer, said timer configured to:
    provide an indication of an expiration of a pre-determined time to said electronic circuit, wherein said electronic circuit is configured to:
      receive said indication of said expiration of said pre-determined time; and
      remove said application of said voltage to said plurality of light emitting sources in response to said received indication.

14. The mouth guard of claim 13, wherein said timer is initiated to said pre-determined time based on said received indication of proximity.

15. A mouth guard comprising:
  a housing comprising:
    a voltage source;
    a plurality of light emitting diodes;
    an electronic circuit;
  a flexible element attached to said housing along a circumference of said housing, said flexible element configured to contact a lower area of a user's face, said flexible element comprising:
    a sensor, said sensor configured to:
    determine at least one of: a proximity to said user's face and a contact with said user's face; and
    generate an indication of at least one of: said proximity to said user's face and said contact with said user's face, wherein said electronic circuit is configured to:
      control an application of a voltage provided by said voltage source to selected one of said plurality of light emitting diodes, wherein said control comprises:
    applying said voltage to said selected one of said plurality of light emitting diodes based on receiving said indication of said at least one of: said proximity to said user's face and said contact with said user's face; and
    remove said voltage from said selected one of said plurality of light emitting diodes based on an absence of said indication of said at least one of: said proximity to said user's face and said contact with said user's face.

16. The mouth guard of claim 15, comprising:
  a timer, said timer configured to:
    determine an expiration of a predetermined time period; and
    generate an indication of said expiration of said time period.

17. The mouth guard of claim 16, wherein said electronic circuit is configured to:
  initiate said timer in response to receipt of said indication of at least one of: a proximity to said user's face and a contact with said user's face; and
  remove said voltage from said selected one of said plurality of light emitting diodes based on receiving said indication of said expiration of said time period.

18. The mouth guard of claim 15, wherein said plurality of light emitting diodes comprises light emitting diodes generating light in at least one of: a non-visible light wavelength range and in a visible light wavelength range.

19. The mouth guard of claim 15, wherein said plurality of light emitting diodes output a light having one of: a substantially same wavelength and a different wavelength.

20. The mouth guard of claim 15, wherein said plurality of light emitting diodes output light at different light intensities.

* * * * *